United States Patent
Averick et al.

(10) Patent No.: US 11,344,241 B2
(45) Date of Patent: May 31, 2022

(54) CONDUCTIVE FIBER WITH POLYTHIOPHENE COATING

(71) Applicants: Allegheny Singer Research Institute, Pittsburgh, PA (US); The Board of Regents for Oklahoma State University, Stillwater, OK (US)

(72) Inventors: Saadyah Averick, Pittsburgh, PA (US); Donald M. Whiting, Gibsonia, PA (US); Bertram Richter, Pittsburgh, PA (US); Boyle Cheng, Mars, PA (US); Toby Larue Nelson, Stillwater, OK (US)

(73) Assignee: Allegheny Singer Research Institute, Pittsburgh, PA (US)

( * ) Notice: Subject to any disclaimer, the term of this patent is extended or adjusted under 35 U.S.C. 154(b) by 135 days.

(21) Appl. No.: 16/646,287

(22) PCT Filed: Sep. 13, 2018

(86) PCT No.: PCT/US2018/050826
§ 371 (c)(1),
(2) Date: Mar. 11, 2020

(87) PCT Pub. No.: WO2019/055617
PCT Pub. Date: Mar. 21, 2019

(65) Prior Publication Data
US 2020/0281497 A1 Sep. 10, 2020

Related U.S. Application Data

(60) Provisional application No. 62/557,947, filed on Sep. 13, 2017.

(51) Int. Cl.
*C09D 5/24* (2006.01)
*C09D 7/40* (2018.01)
*C09D 165/00* (2006.01)
*C08K 3/04* (2006.01)
*A61N 1/05* (2006.01)
(Continued)

(52) U.S. Cl.
CPC ............. *A61B 5/296* (2021.01); *A61B 5/25* (2021.01); *A61N 1/0551* (2013.01); *C08K 3/041* (2017.05); *C09D 5/24* (2013.01); *C09D 7/70* (2018.01); *C09D 165/00* (2013.01); *D06M 11/74* (2013.01); *D06M 15/195* (2013.01); *D06M 15/233* (2013.01); *C08K 2201/001* (2013.01); *C08K 2201/011* (2013.01);
(Continued)

(58) Field of Classification Search
CPC ...................................................... H01M 8/00
See application file for complete search history.

(56) References Cited

U.S. PATENT DOCUMENTS

| 7,972,537 B2 | 7/2011 | Meng et al. | |
| 2006/0052509 A1* | 3/2006 | Saitoh | C08K 3/041 524/496 |

(Continued)

FOREIGN PATENT DOCUMENTS

| CN | 102593342 A | 7/2012 |
| WO | 2017151661 A1 | 9/2017 |

*Primary Examiner* — Alexandre F Ferre
(74) *Attorney, Agent, or Firm* — Fox Rothschild LLP

(57) ABSTRACT

This document discloses an electrically conductive fiber coated with polythiophene and a carbon material. Also disclosed is an article of manufacture incorporating the conductive fiber.

16 Claims, 6 Drawing Sheets

(51) Int. Cl.
  *A61B 5/296* (2021.01)
  *D06M 11/74* (2006.01)
  *D06M 15/19* (2006.01)
  *D06M 15/233* (2006.01)
  *A61B 5/25* (2021.01)
  *D06M 101/06* (2006.01)
  *D06M 101/12* (2006.01)
  *D06M 101/32* (2006.01)

(52) U.S. Cl.
  CPC .... *D06M 2101/06* (2013.01); *D06M 2101/12* (2013.01); *D06M 2101/32* (2013.01); *D06M 2200/00* (2013.01)

(56) References Cited

U.S. PATENT DOCUMENTS

| | | | |
|---|---|---|---|
| 2010/0307791 A1* | 12/2010 | Kim | H01L 51/0021 174/126.1 |
| 2011/0204297 A1 | 8/2011 | Park et al. | |
| 2011/0317240 A1 | 12/2011 | Sotzing et al. | |
| 2014/0303470 A1 | 10/2014 | Tsukada et al. | |
| 2015/0206619 A1 | 7/2015 | Fukui et al. | |

* cited by examiner

A. rr-P3HT/SWCNTs STAINED COTTON

B. rr-P3HT/SWCNTS STAINED POLYESTER

C. rr-P3HT/SWCNTS STAINED SILK

CONDUCTIVE FIBER WITH POLYTHIOPHENE COATING

RELATED APPLICATIONS AND CLAIM OF PRIORITY

This application is a national stage application of, and claims priority to International Patent Application No. PCT/US2018/050826, filed Sep. 13, 2018, which claims priority to U.S. Provisional Application No. 62/557,947, filed Sep. 13, 2017. The disclosures of the priority applications are fully incorporated herein by reference in their entirety.

BACKGROUND

This patent document discloses an electrically conductive fiber coated with a composite of polythiophene and carbon material. Besides an excellent conductivity and mechanical profile, the fiber distinguishes from conventional fibers in terms of its ease and low cost fabrication.

Over the last few decades, electrically conductive fibers (ECFs) have been successfully used in many fields such as medical, sensors, sports, military, aerospace, wearable fabrics and energy applications. Generally, ECFs are made either from 1) intrinsically conductive materials like metals, carbon or conductive polymers or by 2) coating or embedding with electrically conductive materials on conventional insulating materials or less conductive substrates most often cotton, polyester, nylon, and silk. However, metal-based ECFs often have serious drawbacks. For example, coil-like metallic electrodes used in vagal nerve stimulation result in 10-20% incidence of vagal nerve damage. During the past few years, ECFs made from organic material (non-metallic) have emerged as an attractive and promising class of materials for realizing non-metallic interconnects for different clinical applications. This being because of their biocompatibility, better integration, ease of fabrication, light weight and limited magnetic resonance imaging problems compared to the metal involved ECFs. However, organic ECFs obtained from conductive polymer, carbon black, or by coating non-conductive fibers by conductive polymer or carbon black are either limited by their low conductivity, high cost of fabrication or reduced mechanical properties.

Thus, a need exists for improved ECFs that have a desirable conductivity profile. It is further desirable that the ECFs can be fabricated in a manner that is facile, economical and scalable.

SUMMARY

Described herein are a new class of ECFs that have a desirable conductivity and mechanical properties suitable for various fields of applications. Compared to other non-metallic conductive materials, these ECFs are also advantageous in terms of their ease and low cost of fabrication.

An aspect of the embodiments described in the patent document provides an electrically conductive fiber comprising a fiber core and a coating thereon. The coating contains a polythiophene and a conductive carbon material in a ratio ranging from about 1:5 to about 5:1 by weight. The fiber core consists of a single filament thread or a multi-filament fiber thread, which can be fabricated from a synthetic or natural polymer.

In some embodiments, the fiber core consists essentially of cotton, hemp, nylon, silk, jute, flax, ramie, sisal, wool, or any combination thereof. In some embodiments, the fiber core comprises a polymer selected from polylactic acids, polyglycolic acids, polylactide-co-glycolide copolymers, polytrimethylene carbonate, poly-(ε)-caprolactone, poly-dioxanone, polyhydroxyalkanoates, polyphosphasenes, polypropylene fumarates, polyanhydrides, polyorthoesters, polyimides, polyurethanes, polyurethaneureas, perfluoroalkoxy polymers, fluorinated ethylene/propylene copolymers, polyanhydride esters, polysaccharides, polyethylene-lactone copolymers, polyethylene-polyorthoester copolymers, hydrophilic vinyl polymers, phosphoryl cholines, hydroxamates, vinyl furanones, collagen, elastin, keratin, fibrin, and blends, copolymers, homopolymers, and any combination thereof.

In some embodiments, the conductive carbon material is selected from graphene, multi-wall carbon nanotubes, single-wall carbon nanotubes, carbon black, graphite powder, fullerenes and any combination thereof. In some embodiments, the conductive carbon material is composed of single-wall carbon nanotubes.

In some embodiments, the polythiophene is substituted with a C1-10 alkyl substituent. One or more carbon atoms of the C1-10 alkyl substituent are optionally replaced with a heteroatom/group such as 0, S, and amino-C1-5 alkyl. The C1-10 alkyl substituent can be optionally substituted with one or more substituents selected from the group consisting of OC1-5 alkyl, amino-C1-5 alkyl, SC1-5 alkyl, halogen, $NH_2$, OH, SH, C1-5 alkyl, carboxyxlic acid, trimethoxysilane, trihydroxylsilane and phosphonic acid. In some embodiments, the polythiophene contains at least one group inert to the carbon material but capable of forming a bond with the fiber core. The group is selected from the group consisting of hydroxy, amine, carboxylic acid, and thiol. In some embodiments, the polythiophene is poly(3-hexylthiophene).

Another aspect provides an article of manufacture incorporating conductive fibers as described in this document. The conductive fibers described herein may help to overcome the major challenges facing current metal based electrodes that have several drawbacks: damage to nervous systems structures due to stiffness and weight which may lead to nerve end or contorsional damage, heat generation, ionic transfer, cost, and imaging limitations. Coil-like metallic electrodes used in vagal nerve stimulation result in 10-20% incidence of vagal nerve damage. This could be averted using highly malleable, soft electrodes incorporating the conductive fibers described herein. The electrodes composed of a new class of entirely non-metal materials may be used as a monitoring or stimulating agent by placement around the nerve fiber of interest or on the skin surface. Due to the ability to tune the diameter of the electrical conductive fibers, novel configurations can be achieved wherein single nerve bundles can be isolated and monitored by using electrical conductive fibers with diameters of, for example, 1 to 10 microns allowing for precise spatial placement of electrodes on the nerve fibers of interest. Furthermore, the electrical conductive fibers described in this document may be designed to serve as tissue regeneration substrates and integrate cells as a part of the healing process a feature unavailable to metallic electrodes.

A further aspect provides a method of manufacturing the conductive fiber described herein. The method includes the steps of: (a) exposing a fiber thread to a mixture containing a polythiophene and a conductive carbon material in a solvent; and (b) removing the solvent from the fiber thread to obtain the conductive fiber.

In some embodiments, the polythiophene and the conductive carbon material in step (a) have a ratio of about 2:1 by weight. In some embodiments, the carbon material is single wall carbon nanotubes having a concentration ranging from about 0.7 to about 0.9 mg/mL in the solvent. In some embodiments, the solvent is chloroform.

DETAILED DESCRIPTION

Figure 1:
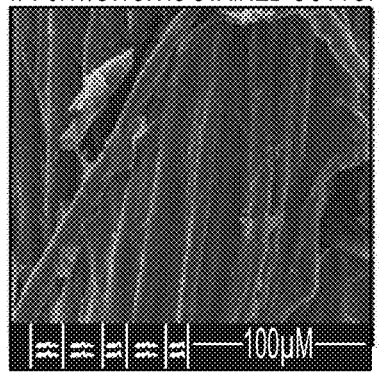
FIG. 1 illustrates scanning electron microscopy (upper) and transmission electron microscopy (lower) images of coated threads obtained after 10 dipping cycles: A) coated cotton (left); B) coated polyester (center); and C) coated silk (right).
Figure 1:
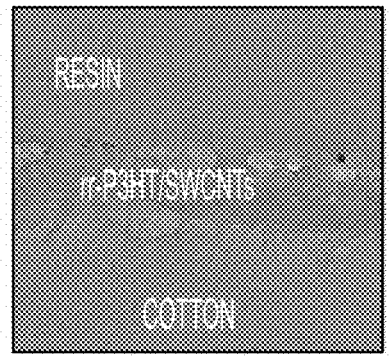
Figure 1:
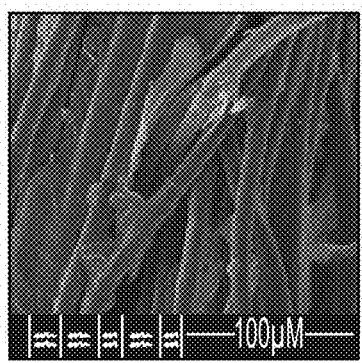
Figure 1:
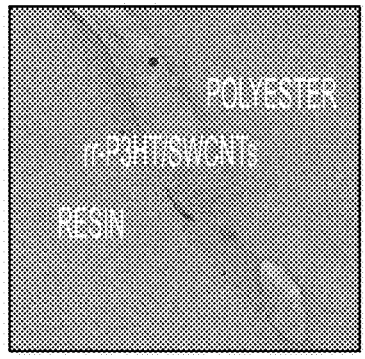
Figure 1:
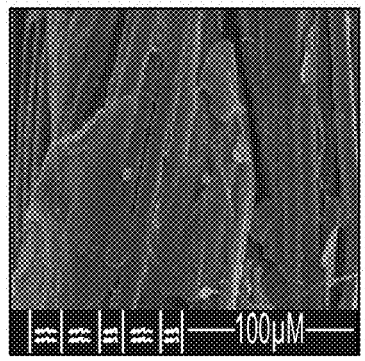
Figure 1:
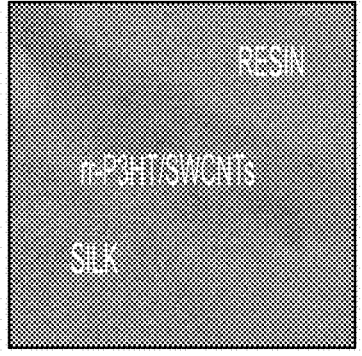

This document discloses electrically conductive organic fibers containing a fiber core coated with at least two intrinsically conductive materials. In comparison with conventional fibers, the fibers described herein are lighter, more flexible, and highly conductive. In addition, the fibers described herein can be manufactured with biocompatible components at a much lower cost.

While the following text may reference or exemplify specific embodiments of a conductive fiber or a method of fabricating the fiber, it is not intended to limit the scope of the conductive fiber to such particular reference or examples. Various modifications may be made by those skilled in the art, in view of practical and economic considerations, such as the amount of the carbon material in the fiber and its ratio relative to the conductive polymer.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "about" as used herein refers to the referenced numeric indication plus or minus 10% of that referenced numeric indication.

An aspect of the document provides a conductive fiber comprising a fiber core and a coating thereon. The coating includes a polythiophene and a conductive carbon material in a ratio ranging from about 1:5 to about 5:1 by weight. No particular restriction is placed on the length of the conductive fiber, other than practical considerations based on manufacturing considerations and intended use. Further, no restriction is placed on the cross-sectional shape of the conductive fiber, providing the desirable properties such as flexibility and stretchability are not adversely affected. For example, the conductive fiber can have a cross-sectional shape of a circle, ellipse, square, rectangle, or irregular shape.

Fibers, synthetic or natural, are a class of materials that includes continuous filaments or are in discrete elongated pieces, similar to lengths of thread. They can be spun into filaments, string or rope, used as a component of composite materials, or matted into sheets to make products such as paper or felt. In some embodiments, the fiber core consists of a single filament fiber thread. In some embodiments, the fiber core consists of multi-filament fiber thread, which can be made from fibers spun, woven, knitted, crocheted, knotted, pressed, plied, or the like from multiple filaments.

The material for the fiber thread core can be doped with a metal. Examples of electrically conductive metals that can be used as a dopant include silver, copper, gold, iron, aluminum, zinc, nickel, tin, and combinations comprising at least one of the foregoing metals. Iron and iron alloys such as stainless steel (an alloy of carbon, iron, and chromium) can also be used.

In some embodiments, the fiber core consists of one or more non-conductive materials, and has a resistivity of more than about 10, more than about 20, or more than about 50, or more than about 100 kohm·cm. Non-limiting examples of such non-conductive materials include natural materials (e.g., cotton, silk, hemp, jute, flax, ramie, sisal, hair, fur, and wool) and synthetic organic polymers (e.g., poly(amide) (nylon), poly(ethylene), poly(ester), poly(acrylic), polyurethane (spandex), poly(lactide), and the like). In some embodiments, the fiber core contains one or more polymers selected from polylactic acids, polyglycolic acids, polylactide-co-glycolide copolymers, polytri-methylene carbonate, poly-($\varepsilon$)-caprolactone, poly-dioxanone, polyhydroxyalkanoates, poly-phosphasenes, polypropylene fumarates, polyanhydrides, polyorthoesters, polyimides, poly-urethanes, poly-urethaneureas, perfluoroalkoxy polymers, fluorinated ethylene/propylene co-polymers, polyanhydride esters, polysaccharides, polyethylene-lactone copolymers, polyethylene-polyorthoester copolymers, hydrophilic vinyl polymers, phosphoryl cholines, hydroxamates, vinyl furanones, collagen, elastin, keratin, fibrin, and blends, copolymers, homopolymers, and any combination thereof.

As mentioned above, a single filament can be woven, knitted, crocheted, knotted, pressed, or plied to form a multi-filament fiber. It is also possible to have multiple nonconductive fibers formed into a yarn, and then used in combination with a conductive material in the fiber core.

In some embodiments, the fiber core consists of one or more non-conductive materials and the coating comprises a carbon material and a polythiophene. In some embodiments, the fiber core consists of a non-conductive material and the coating consists essentially of a carbon material and a polythiophene.

The conductive carbon material generally has a resistivity of less than about 20, less than about 10, less than about 5, or less than about 1 kohm·cm. Non-limiting examples include graphene, multi-wall carbon nanotubes, single-wall carbon nanotubes, carbon black, graphite powder, fullerenes, and any combination thereof. In some embodiments, the conductive carbon material consists essentially of single-wall carbon nanotubes.

The polythiophene in the coating can be substituted or unsubstituted. In some embodiments, the polythiophene is substituted with a C1-10 alkyl substituent. One or more carbon atoms of the C1-10 alkyl substituent are optionally replaced with a heteroatom/group selected from O, S, and amino-C1-5 alkyl. Meanwhile, the C1-10 alkyl substituent is optionally substituted with one or more substituents selected from the group consisting of OC1-5 alkyl, amino-C1-5 alkyl, SC1-5 alkyl, halogen, NH2, OH, SH, C1-5 alkyl, carboxyxlic acid, amide and perfluoroalkyl. In some embodiments, the polythiophene is poly(3-hexylthiophene). A "C1-10 alkyl substituent" refers to an alkyl substituent, which can have 1, 2, 3, 4, 5, 6, 7, 8, 9, or 10 carbons. Similarly, a "C1-5 alkyl substituent" can have any number of carbons from 1 to 5, inclusive.

In some embodiments, the substituents of the polythiophene are inert to the carbon material but are reactive enough to interact with a chemical group on the fiber core. Such interaction can be through, for example, van der Waals forces, hydrogen bonding, ionic interaction, or the formation of a covalent bond. In some embodiments, the polythiophene contain one or more substituents or groups selected from the substituents of hydroxy, amine, carboxylic acid, amide thiol, sulfonate, and perfluoroalkyl, which are capable of forming a bond with a chemical group on the material of the fiber core. Similarly, the fiber core can contain one or more functional groups selected from hydroxy, amine, amide carboxylic acid, thiol, sulfonate, trimethoxysilane, trihydroxylsilane and phosphonic acid.

The coating and/or fiber core can each independently further include one or more additional conductive polymers such as conjugated polymers. Non-limiting examples include poly(pyrrole), poly(aniline), poly(acetylene), poly(p-phenylene vinylene) (PPV), poly(3,4-ethylene dioxythiophene)-poly(styrene sulfonate) (PEDOT-PSS), and the like.

The ratio between the polythiophene and the conductive carbon material can be adjusted depending on the manufacturing conditions and the desired use of the conductive fiber. In some embodiment, the ratio is pre-determined such that the conductive fiber exhibits an electrical resistivity of less than about 2, less than about 1, less than about 0.8, less than about 0.7, less than about 0.6, less than about 0.5, less than about 0.4, less than about 0.3, less than about 0.2, or less than about 0.1 ohm·cm. The ratio between the polythiophene and the conductive carbon material can range from about 1:10 to about 10:1 by weight. Examples of the ratio include about 1:8, 1:6, 1:4, 1:2, 1:1, 2:1, 4:1, 6:1, and 8:1.

The length and diameter of the conductive fiber depend on the intended use and the specific composition of the fiber core and its coating. In some exemplary embodiments, the diameter of the fiber ranges from about 1 to about 10,000 microns, from about 1 to about 1,000 microns, from about 1 to about 100 microns, from about 50 to about 500 microns, from about 100 to about 400 microns, from about 100 to about 300 microns, from about 200 to about 300 microns, from about 200 to about 300 microns, from about 0.1 to about 20 microns, from about 0.5 to about 20 microns, from about 1 to about 15 microns, from about 1 to about 10 microns, or from about 1 to about 5 microns.

Another aspect of the document provides an article of manufacture containing the conductive fibers described herein, which are of great application in many fields such as medical, sensors, sports, military, aerospace, wearable fabrics and energy applications. Besides the desirable electrical conductivity and mechanical properties, advantages of the conductive fibers described herein also include low cost fabrication, durability and ease of adaptability. Devices incorporating these fibers can be used in fields such as motion capture, electrotherapy, photovoltaic, field effect transistor, pressure and chemical sensor, monitoring power and signals for electrocardiogram (EKG), EMG and electroencephology (EEG).

The electrical conductive fibers described in this the patent document overcome some or all of the myriad of challenges currently facing metal electrodes composed of metal fibers or other non-metal materials. For example, the enhanced flexibility, resistance to tearing, and non-irritancy allow the fibers to be configured in unique ways and onto unique substrates to yield wearable electronics with features matching natural fabrics. Because of its biocompatibility, the fibers described herein are also able to deliver changes in electrical pulse and current without causing damages to nerves for use in nerve stimulators. Thus, electrodes can be fabricated onto thin polymeric fibers enabling direct placement and securing of the electrode on nerve fibers. Small nerve fibers and different fiber types can be selectively recorded from and stimulated by directly securing the electrode to the fiber. Further, due to the unique properties of being non-swelling, biodegradable and inert to biological media (e.g. serum, enzymes, proteins), the fibers can be used in implantation and employed in minimally invasive endoscopic procedures.

Non-limiting examples of devices or components incorporating the conductive fibers described herein include transistor, photovoltaic cells, light emitting diodes, RFID tags, rectifiers, nerve cell replacement, implantable electrodes, IR imager, memory chips, and biosensors.

Another aspect of the document provides a method of manufacturing the above-described electrically conductive fiber. The method generally includes the steps of: (a) exposing a fiber thread to a solution containing a polythiophene and a conductive carbon material in a solvent; and (b) removing the solvent from the fiber thread.

The sequence of steps (a) and (b) can be repeated to achieve a desirable coating of the fiber thread. Any means of exposing the fiber thread to the solution can be practiced as long as a desirable coating is achieved. For example, the fiber thread core can be submerged into the solution for an extended period of time while the solution is agitated to maximize the physical interaction between the components of the solution and the thread. Alternatively, the solution can be sprayed to the thread. Removal of the solvent can be accomplished by for example, heating, air drying, vacuuming, or any combination of these processes. After the solvent is removed or evaporated, the spraying and solvent removal can be repeated.

Each of the polythiophene and the conductive carbon material can be partially or completely dissolved in the solution. In cases of these materials partially being dissolved in the solution, a uniform suspension is desirable for coating the fiber thread core. Various known techniques such as shaking, sonicating can be used to mix the polythiophene and the conductive carbon material uniformly in the solution. In some embodiments, heating or microwaving can be applied to promote the even distribution of the materials into the solution.

The polythiophene may be soluble in the solvent, which can be for example, chloroform, dichloromethane, chlorobenzene, dichlorobenzene trichlorobenzene, tetrahydrofuran, toluene, N,N-dimethylformamide acetone, alcohol, ethyl acetate or any combination of these. Removal of the solvent can be accomplished by for example, heating, air drying, vacuuming, or any combination of these processes.

As explained above, the fiber thread serves as a core and can be of a single filament or multi-filaments. In some embodiments, the fiber core is made of of non-conductive materials include natural materials (e.g., cotton, silk, hemp, jute, flax, ramie, sisal, hair, fur, and wool) and synthetic organic polymers (e.g., poly(amide) (nylon), poly(ethylene), poly(ester), poly(acrylic), polyurethane (spandex), poly(lactide), and the like). In some embodiments, the fiber core contains one or more polymers selected from polylactic acids, polyglycolic acids, polylactide-co-glycolide copolymers, polytrimethylene carbonate, poly-(ε)}-caprolactone, poly-dioxanone, polyhydroxyalkanoates, polyphosphasenes, polypropylene fumarates, polyanhydrides, polyorthoesters, polyimides, polyurethanes, polyurethaneureas, perfluoroalkoxy polymers, florinated ethylene/propylene copolymers, polyanhydride esters, polysaccharides, polyethylene-lactone copolymers, polyethylene-polyorthoester copolymers, hydrophilic vinyl polymers, phosphoryl cholines, hydroxamates, vinyl furanones, collagen, elastin, keratin, fibrin, and blends, copolymers, homopolymers, and combinations thereof.

The polythiophene in the coating can be substituted or unsubstituted. In some embodiments, the polythiophene is substituted with a C1-10 alkyl substituent, wherein one or more carbon atoms of the C1-10 alkyl substituent are optionally replaced with a heteroatom/group selected from O, S, and amino-C1-5 alkyl. Meanwhile, the C1-10 alkyl is optionally substituted with one or more substituents as explained above. In some embodiments, the polythiophene contain one or more substituents selected from the substituents of C1-10 alkyl, hydroxy, amine, amide, carboxylic acid, thiol, sulfonate, trimethoxysilane, trihydroxylsilane and phosphonic acid, which are capable of interacting with a chemical group on the material of the fiber core and form a linkage (e.g ester, amide, ether, sulfonamide, etc).

The conductive carbon material in the solution is as described above. In some embodiments, the conductive carbon material consists essentially of single-wall carbon nanotubes.

The ratio between the polythiophene and the conductive carbon material has a significant impact on the conductivity of the resulting fiber. The ratio of the polythiophene to the conductive carbon material by weight in the solution can range from about 1:10 to about 10:1 by weight. Examples of the ratio include about 1:8, 1:6, 1:4, 1:2, 1:1, 2:1, 4:1, 6:1, and 8:1. In some embodiments, the solution consists essentially of the poly(3-hexylthiophene) and single wall carbon nanotubes, which are in a ratio of about 2:1 by weight.

The concentration of the individual component in the solution may impact the conductivity of the final product. Generally, the carbon material has a concentration in the solvent or suspension system ranging from about 0.1 mg/mL to about 5 mg/mL. Non-limiting examples of the concentration includes about 0.2, about 0.4, about 0.6, about 0.8, about 1.0, about 1.2, about 1.4, about 1.6, about 2.0, about 3.0, and about 4.0 mg/mL. In some embodiments, the carbon material is single wall carbon nanotubes. The method allows for fabrication of the organic conductive fibers with comparatively less resistivity using much fewer amounts of single walled carbon nanotubes (SWCNTs) than what has been reported in the literature while also retaining good mechanical properties to be used for a variety of applications.

EXAMPLES

Example 1

Materials and Instrumentations: Regioregular poly(3-hexylthiophene) rr-P3HT was synthesized using the previously reported procedure (ref). SWCNTs (purity >95%) was purchased from Aldrich. The resistivity measurements were characterized using our in-house thread measuring apparatus connected to a multimeter. Scanning electron microscopy (SEM) was used to investigate the morphology of the uncoated and coated threads. The morphology of the threads was probed with an FEI Quanta 600 SEM with Evex EDS system (FEI, Hillsboro, Oreg.). The SEM samples were prepared by mounting a piece of coated thread on an aluminum stub. Samples were then coated with a very thin layer of palladium/gold metal deposited using a MED 010 sputter coater (Balzers, Oberkochen, Germany) to make them conductive. The mechanical strength of the conductive threads was characterized by means of stress-strain measurements performed on a TA instrument DMA Q800. The stress applied varied from 0 to 18 N with the linear ramp force 1.00 N/min Strain was expressed as percentage elongation with respect to the sample's original length.

Method of Fabrication: The conductive ink was prepared by dispersing single-walled carbon nanotubes (SWCNTs) into chloroform using regioregular poly(3-hexylthiophene) (rr-P3HT). The preparation of the conductive ink began by adding SWCNTs to the rr-P3HT solution in CHCl3. The resulting mixture was ultrahigh sonicated for 30 minutes maintaining a temperature of 0° C. A dipping and drying technique was utilized to coat the thread with the conductive ink. After coating, the threads were oven dried for 15 minutes at 100° C.

Optimization of Number of Dipping Cycles, SWCNTs to P3HT Ratio and Concentration of SWCNTs: Cotton threads were used for all of these optimization. The cotton thread was completely submersed into the conductive ink and then oven dried. The resitivity was then measured using our thread measuring apparatus attached to a multimeter. This process was repeated 20 times and the resistivity data was plotted against the number of dipping cycles. The cotton threads were found to be conductive after one dipping and drying cycle. The cotton thread became less resistant with the number of dipping cycles however after 10 dipping cycles, the resistance of the thread remained constant at 0.45 kohm/cm.

To optimize the concentration of the SWCNTs, three different concentrations of SWCNTs (0.5 mg/mL, 0.8 mg/mL and 1.2 mg/mL) were used to prepare the conductive ink while keeping the SWCNT:P3HT ratio the same (1:2). It was found that 0.8 mg/mL of SWCNTs yield the lowest of 0.45 kiloOhm/cm. The resistance of the threads was found to increase with both increased and decreased SWCNT concentration.

TABLE 1

Electrical resistance per length of the coated cotton obtained by varying concentration of SWCNTs keeping the SWCNT:P3HT ratio same

| SWCNT:P3HT | Concentration of SWCNT | Resistance (kohm/cm) |
| --- | --- | --- |
| 1:2 | 0.5 mg/mL | 0.90 |
| 1:2 | 0.8 mg/mL | 0.45 |
| 1:2 | 1.2 mg/mL | 1.02 |

Once the concentration of SWCNTs was optimized, then the ratio of the SWCNT to P3HT was investigated by keeping the concentration SWCNTs constant (0.8 mg/mL). It was found that 1:2 ratio of SWCNT to P3HT provide the low resistance.

TABLE 2

Electrical resistance per length of the coated cotton obtained by changing the SWCNT:P3HT ratio keeping the concentration of SWCNTs same

| SWCNT:P3HT | Concentration of SWCNT | Resistance (kohm/cm) |
|---|---|---|
| 1:1 | 0.8 mg/mL | 0.54 |
| 1:2 | 0.8 mg/mL | 0.45 |
| 1:3 | 0.8 mg/mL | 0.76 |

After the optimization of number of dipping cycles, ratio of SWCNT to P3HT and concentration of SWCNT, the optimized conditions were used for further fabrication of all the organic conductive threads.

Characterization of Organic Conductive Threads: Three different organic threads made from cotton, silk and polyester (both natural and synthetic organic threads) were used to fabricate the organic conductive threads using the optimized conditions. Each conductive thread was then characterized by electrical measurements, scanning electron microscopy (SEM), Transmission electron microscopy (TEM) stress-strain measurements and Raman spectroscopy.

Figure 2:
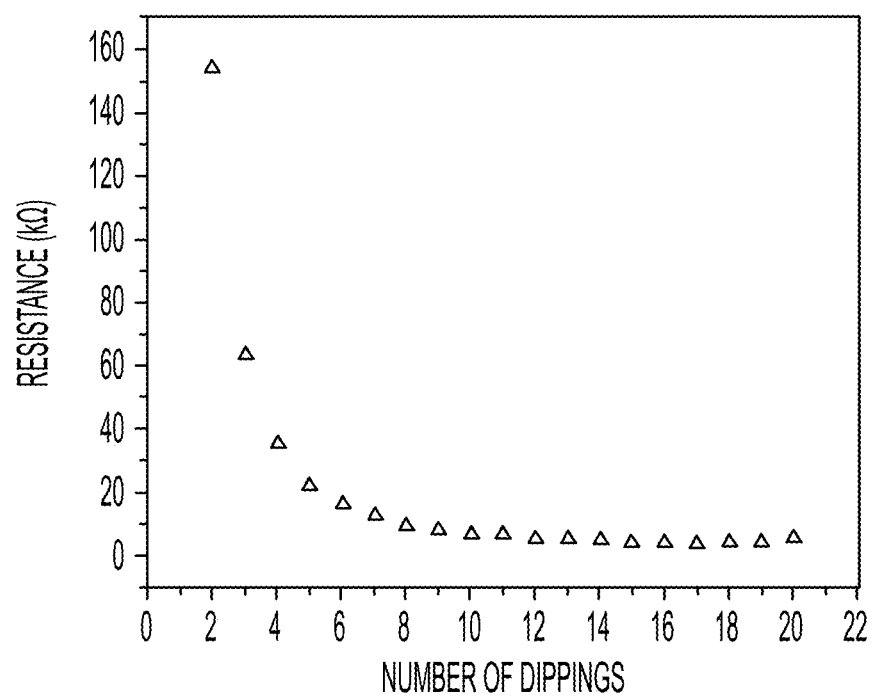
FIG. 2 illustrates the correlation between conductive fiber resistance and the number of dip coating procedures used in its preparation.

Electrical measurements: The resistance of the conductive organic threads was measured by using a thread measuring apparatus attached to a multimeter (FIG. 2). The resistances of the uncoated threads were too high to be measured by the given apparatus. The results are shown in Table 3.

TABLE 3

Electrical resistance of the three different coated threads

| Sample (Coated Samples) | Resistance* |
|---|---|
| SA-22-77-Cotton | 0.50 kohm/cm |
| SA-22-77-Silk | 0.65 kohm/cm |
| SA-22-77-Polyester | 0.73 kohm/cm |

*The data shows the average of three different conductive threads of each type.

The morphology of the three conductive threads was observed by scanning electron microscopy (upper images in FIG. 1) and the coated threads obtained after 10 dipping cycles. It is clearly seen on the SEM images that the conductive composite has covered the exterior of every strand of each thread and has also filled the gap between strands. Also observed was an increase in diameter of the coated cotton and silk threads with conductive composite but a slight decrease in the case of polyester TEM images of the materials (Lower images in FIG. 1) provide further evidence of the presence of SWCNTs on the surface of the underlying fiber. TEM images in FIG. 1 clearly show the stained region on each type of fibers and also show the presence of carbon nanotubes which appeared as darker spots on the stained region.

Figure 3:
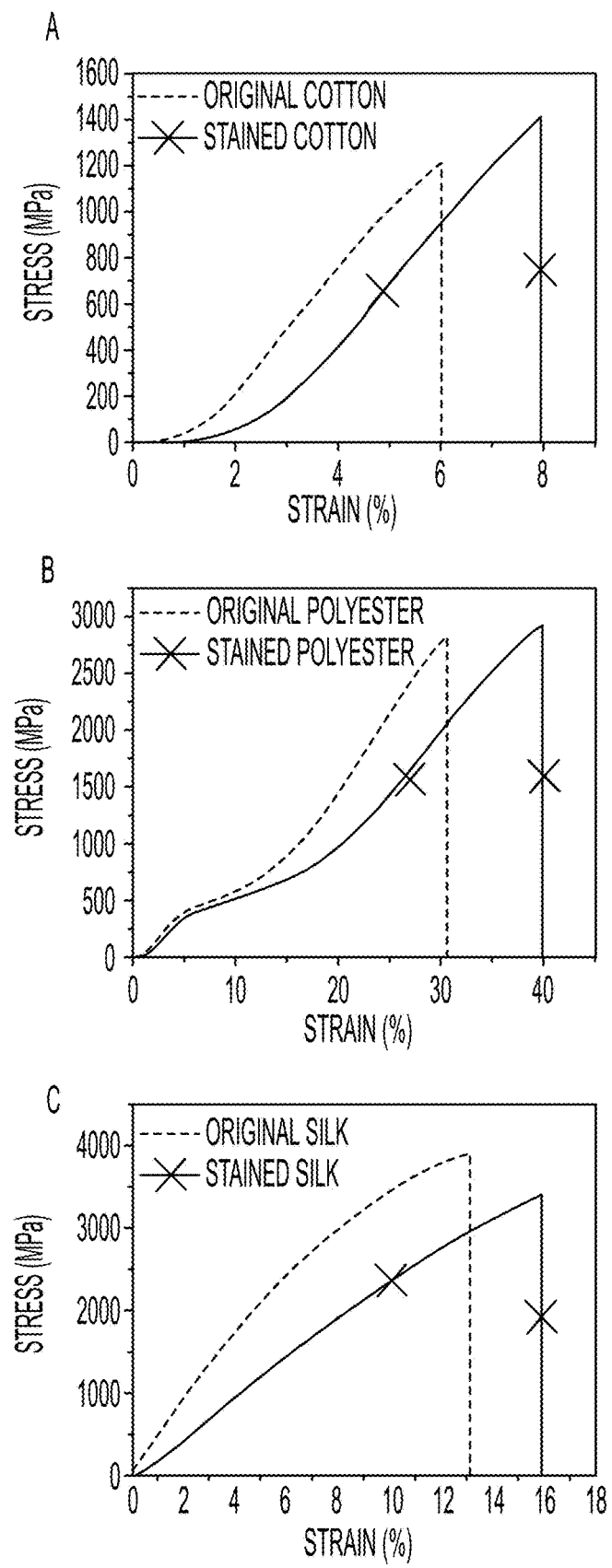
FIG. 3 illustrates stress-strain plots for; A) original and coated cotton, B) original and coated polyester and C) original and coated silk.

Stress-strain measurements: The mechanical strength of the conductive threads was characterized by means of stress-strain measurements performed using a TA instrument DMA Q800. Mechanical parameters: Young's modulus; ultimate breaking stress; and elongation at break were acquired using 3 different fibers of the same type and the mean values of the parameters for all original and coated threads are reported in Table 4. Stress-strain plots are shown in FIG. 3.

TABLE 4

Mechanical data of the coated threads

| Samples | Young's Modulus (MPa) | Ultimate Breaking Stress (MPa) | Elongation at Break Point (%) |
|---|---|---|---|
| Original Cotton | 296 ± 36 | 1214 ± 173 | 6.0 ± 0.3 |
| Coated Cotton | 257 ± 17 | 1402 ± 30 | 7.9 ± 0.2 |
| Original Silk | 305 ± 32 | 3920 ± 34 | 13.1 ± 0.9 |
| Coated Silk | 241 ± 23 | 3414 ± 69 | 15.9 ± 0.3 |
| Original Polyester | 127 ± 10 | 2833 ± 127 | 30.7 ± 0.5 |
| Coated Polyester | 76 ± 4 | 2915 ± 289 | 40.0 ± 1.3 |

Based on the data, two main observations were made. First, the maximum elongation of the material before breaking was found to increase in the coated fibers compared to the original, uncoated material. This indicates that the main mechanical property of interest, such as flexibility, for evaluating the ability of the fiber to be woven or knitted was preserved in the coated fibers.

Second, we observed a decrease in Young's modulus for each coated fiber, indicating that the conductive composite coating decreased the stiffness of the thread. This property of the modified fibers may be attributed to a lubricant effect of the coating assembly that seems to enable fiber strands to more easily slide on one another following the application of a mechanical stimulus.

These results indicate that the coated threads are more flexible and less stiff than their original counterparts. However, these coated threads still possess the mechanical properties of interest for their ability to be woven or knotted for their application in making smart fabrics and in non-metallic interconnects for clinical applications.

Figure 4:
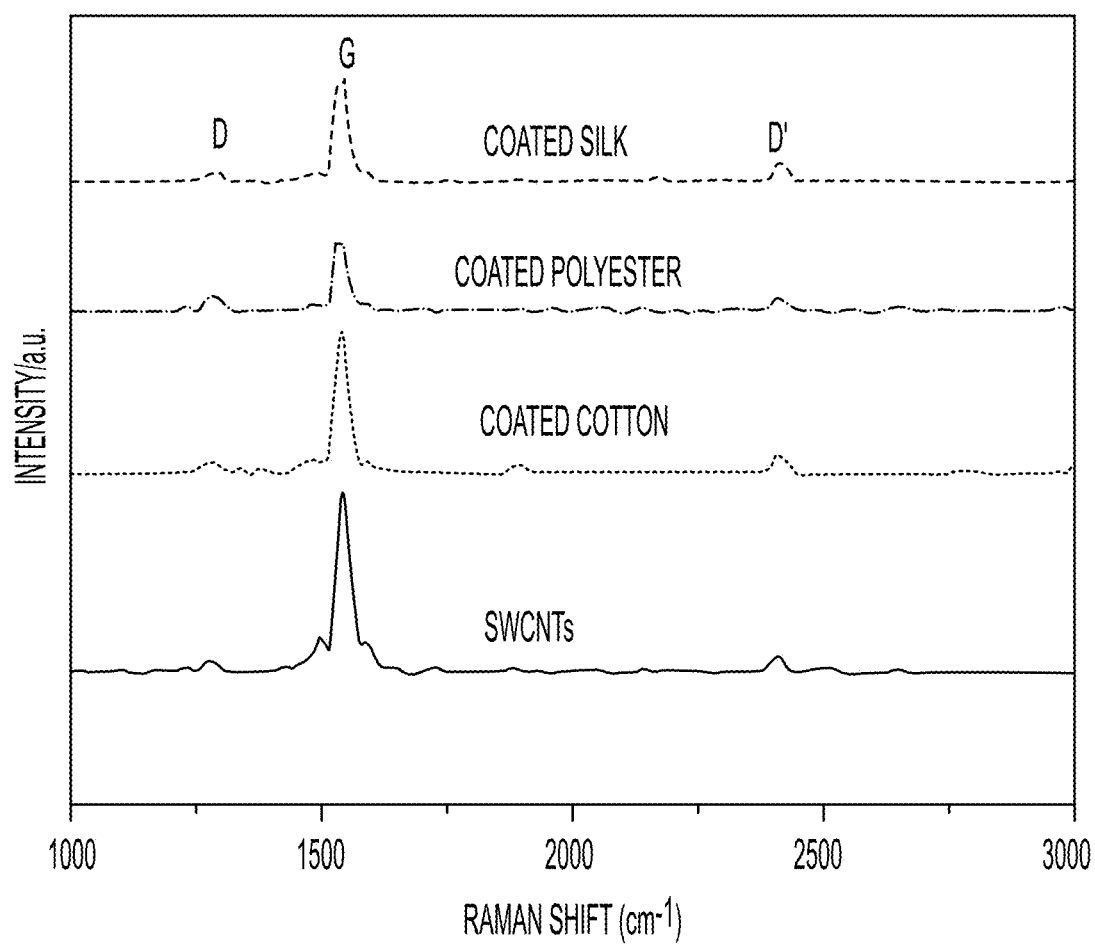
FIG. 4 compares Raman spectra of single wall carbon nanotubes to those of modified threads, illustrating the presence of carbon on the fibers.
Figure 5:
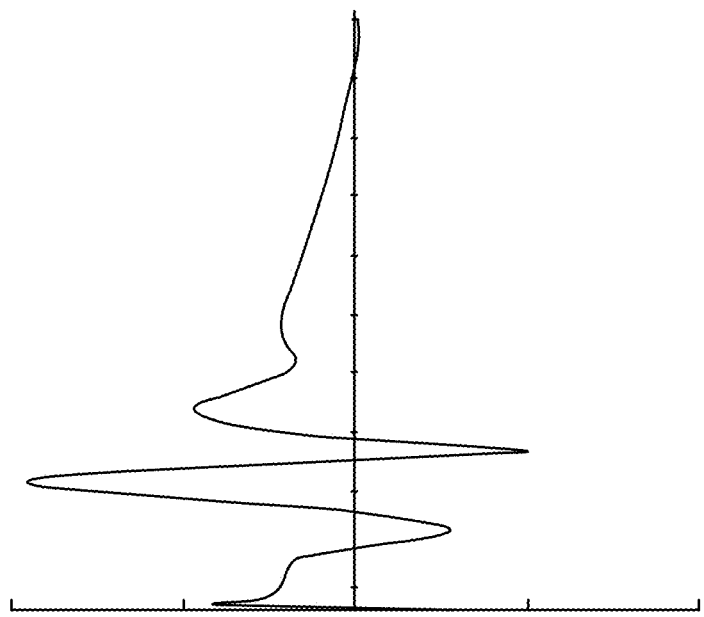
FIG. 5 illustrates the evoked electromyography (EMG) of tibialis anterior when using A) a commercial electrode and B) conductive polyester fiber to stimulate the sciatic nerve in a rat.
Figure 5:
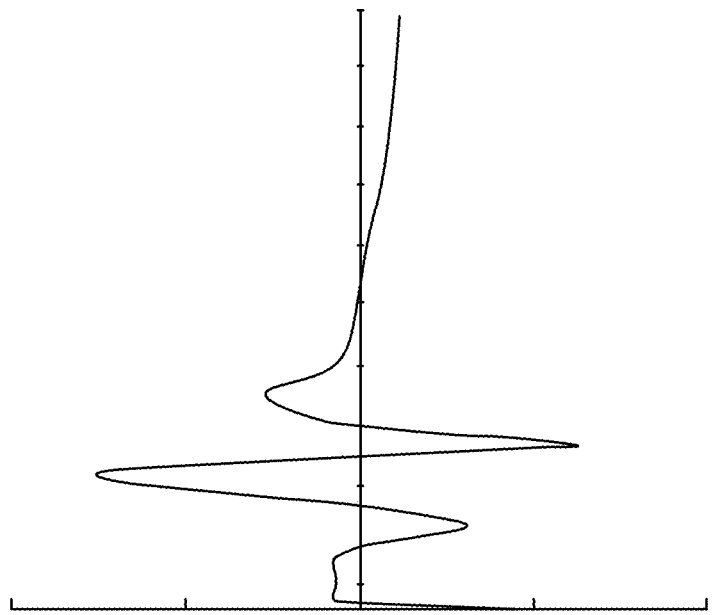

In order to provide further evidence for the presence of SWCNTs in the conductive polymers, the resulting fibers were examined using Raman spectroscopy. Raman spectra of the three organic conductive threads and SWCNTs are shown in FIG. 4. The characteristic D-band (~1277 cm-1) and G-band (~1540 cm-1) for SWCNTs can be clearly observed on all the three organic ECFs. Additionally, second order band (~2407 cm-1) is also clearly identified in all the organic ECFs, implying the presence of SWCNTs in all coated fibers.

Example 2

When poly(3-hexylthiophene) rr-P3HT/SWCNT conductive silk, cotton, and polyester fibers (~0.2 mm) were used to measure EKG and EMG, signals were observable. No signal was seen when uncoated silk, cotton, or polyester was used (signal read as open circuit). The fibers can be used either on the skin or implanted.

The resistivity and conductivity of the organic conductive fibers were measured by passing a charge through the fibers from a calibrated current source and the voltage was measured on an oscilloscope.

TABLE 5 resistivity and conductivity of the organic conductive fibers

| R (ohms) | L (cm) | diameter (cm) | radius (cm) | r² (cm²) | A (cm²) | ρ (ohm · cm) | σ (S/cm) |
|---|---|---|---|---|---|---|---|
| SA-22-77-Cotton | | | | | | | |
| 6170 | 10 | 0.0236 | 0.0118 | 0.0001392 | 0.0004374 | 0.269898 | 3.705 |
| 6000 | 10 | 0.0236 | 0.0118 | 0.0001392 | 0.0004374 | 0.262461 | 3.810 |
| 6100 | 10 | 0.0236 | 0.0118 | 0.0001392 | 0.0004374 | 0.266836 | 3.747 |
| 6000 | 10 | 0.0236 | 0.0118 | 0.0001392 | 0.0004374 | 0.262461 | 3.810 |
| SA-22-77-Polyester | | | | | | | |
| 13280 | 10 | 0.0237 | 0.01185 | 0.0001404 | 0.0004412 | 0.585848 | 1.706 |
| 13050 | 10 | 0.0237 | 0.01185 | 0.0001404 | 0.0004412 | 0.575701 | 1.737 |
| 12660 | 10 | 0.0237 | 0.01185 | 0.0001404 | 0.0004412 | 0.558496 | 1.790 |
| 12500 | 10 | 0.0237 | 0.01185 | 0.0001404 | 0.0004412 | 0.551438 | 1.813 |
| SA-22-77-Silk | | | | | | | |
| 14690 | 10 | 0.02309 | 0.011545 | 0.0001333 | 0.0004187 | 0.615120 | 1.625 |
| 14770 | 10 | 0.02309 | 0.011545 | 0.0001333 | 0.0004187 | 0.618469 | 1.616 |
| 14690 | 10 | 0.02309 | 0.011545 | 0.0001333 | 0.0004187 | 0.615120 | 1.625 |
| 14530 | 10 | 0.02309 | 0.011545 | 0.0001333 | 0.0004187 | 0.608419 | 1.643 |

*Resistance R (ohms)
Length of the thread L (cm)
Diameter of the thread (from SEM image)
Radius of the thread r (cm)
Cross sectional Area A (A = πr2, cm2)
Resistivity = Resistance × Area/length (ρ = RA/L)
Electrical conductivity (σ) = 1/ρ
*The resistivity for each of uncoated cotton, uncoated polyester and uncoated silk is too high to measure.
When I is 1 mA, V is greater than 60 volts. R is thus greater than 6 kohm/cm.

Example 3

The fibers of Example 2 were used to record the electromyogram and electrocardiogram of a 30 year old male using a skin surface recording. The skin of the subject's left palm was cleaned using an alcohol swap. The skin was then prepared via abrasion with NuPrep gel. Excess NuPrep gel was removed, and two approximately 15 mm balls of Ten20 paste were pressed onto the skin. One ball was placed above the abductor pollicis muscle and the other was placed above the flexor digiti minimi muscle. An area of the subject's right palm over the flexor digiti minimi was prepared in the same manner.

The subject's forearm was then cleansed with alcohol and the skin was prepared with NuPrep as described above. A Grass 9 mm Disposable Gold Cup electrode was filled with Ten20 paste and applied to the subjects forearm and further secured with Transpore adhesive tape (3M).

Both halves of two Grass Gold Cup EEG Ear Clips were liberally filled with Ten20 paste so that the collections of paste completely merged when the clips were closed. Prior to clip closure, the ends of two approximately 10 cm threads of the same type were loaded (one each) into the clips. The remaining exposed ends were each pressed into one of the mounds of Ten20 paste on the subject's left palm, and the paste was molded so it completely encased these ends.

A single channel of EMG was established referencing electrode 1 to electrode 2. The ends of the clip electrodes were inserted into the corresponding holes in the acquisition box. Electrode impedances were then checked and logged. A notch filter was applied to all modalities prior to data collection.

The following procedure was performed for all thread types in pairs consisting of the nanotube coated version followed by the uncoated control of the same material.

The pieces of thread were each secured in one of the two clip electrodes;

The free thread ends were placed into the Ten20 paste on the subject's left palm;

The clip electrodes were inserted into the acquisition box in electrode positions 1 and 2;

Impedances were checked and logged;*

*Electrode impedances over 50 kOhms register as "Open" channels on the Xltek hardware.

Recording of EMG activity was initiated with the subject's hand relaxed;

The subject was asked to move his thumb, then relax;

The subject was asked to abduct his fifth digit, and then relax;

Recording was paused while the thread imbedded in the Ten20 paste over the left flexor digiti minimi was transferred and imbedded into the Ten20 paste on the right palm;

Electrode impedances were again measured and recorded; and

EKG data were recorded with the left abductor pollicis referenced to the right flexor digiti minimi.

Example 4

A 2 year old Sprague Dawley rat was anesthetized and thermoregulated. Depth of anesthesia was monitored with response to stimulus and bradypnea. The area over the left groin was clipped and prepped. Sharp dissection was used to expose the neurovascular bundle in the groin. The sciatic nerve was separated from vascular structures.

A ground electrode was placed in subcutaneous tissue. A stimulation anode was placed medial to ground in subcutaneous tissue and a stimulation cathode was directly applied to the separated sciatic nerve. Recording electrodes were placed in the left tibialis anterior muscle in bipolar montage. (Ambu Neuroline subdermal needle electrode 12×0.40 mm, Ballerup, Denmark).

The sciatic nerve was stimulated with increasing current starting at 0 mA and increased in 0.1 mA increments until compound muscle action potential (CMAP) was observed.

Stimulus frequency was set at 5.1 Hz and Pulse at 200 micro seconds. The threshold was determined to be 0.9 mA. The evoked EMG was then recorded at 1 mA.

The stimulation cathode was then replaced with coated polyester fiber attached to a Grass 10 mm gold cup electrode (Natus, Middleton, Wis., USA) with Ten 20 conductive paste (Weaver, Aurora, Colo., USA) at the interface. The fiber was wrapped around the sciatic nerve, avoiding contact with any other tissue. The sciatic nerve was again stimulated with increasing current starting at 0 mA and increased in 0.1 mA increments until compound muscle action potential (CMAP) was observed. Stimulus frequency and Pulse matched the prior demonstration. The threshold was again reached at 0.9 mA and the evoked EMG was recorded at 1 mA. All recordings were obtained using NeuroNet VI software (Computational Diagnostics Inc., Pittsburgh, Pa., USA).

It was demonstrated near identical evoked EMG recording by signal strength and morphology (1383 micro Volts vs 1459 micro Volts) demonstrating the potential to use coated fibers for direct internal stimulation of peripheral nerves.

Example 5

Gold cup electrodes were placed between the first and second digits of bilateral hands of a healthy 35 year old male in recumbent position after cleaning the skin over the anterior forearm and pads of first and second digits with alcohol. A resting EKG was recorded across extremities and the maximum displacement of 4 separate PQRS complexes was recorded as 653 µV, 726 µV, 762 µV, 685 µV; with an average displacement: 707 µV.

The setup was replicated using coated polyester fibers between the first and second digits of bilateral hands. A resting EKG was recorded across extremities and maximum displacement of 4 separate PQRS complexes was recorded as 605 µV, 601 µV, 532 µV, 609 µV; with an average displacement: 587 µV.

Figure 6:
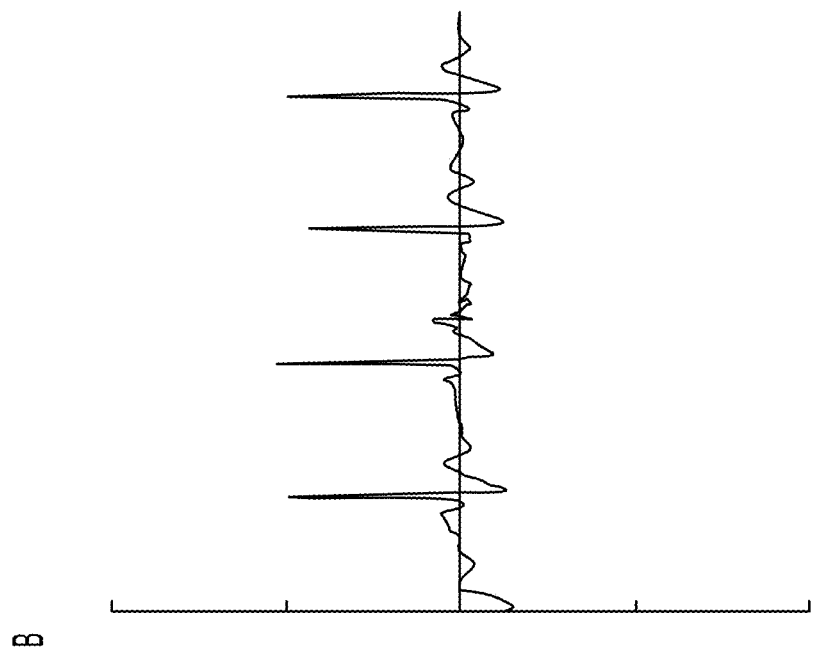
FIG. 6 demonstrates very similar EKGs taken using A) commercial electrodes and B) conductive polyester fibers.
Figure 6:
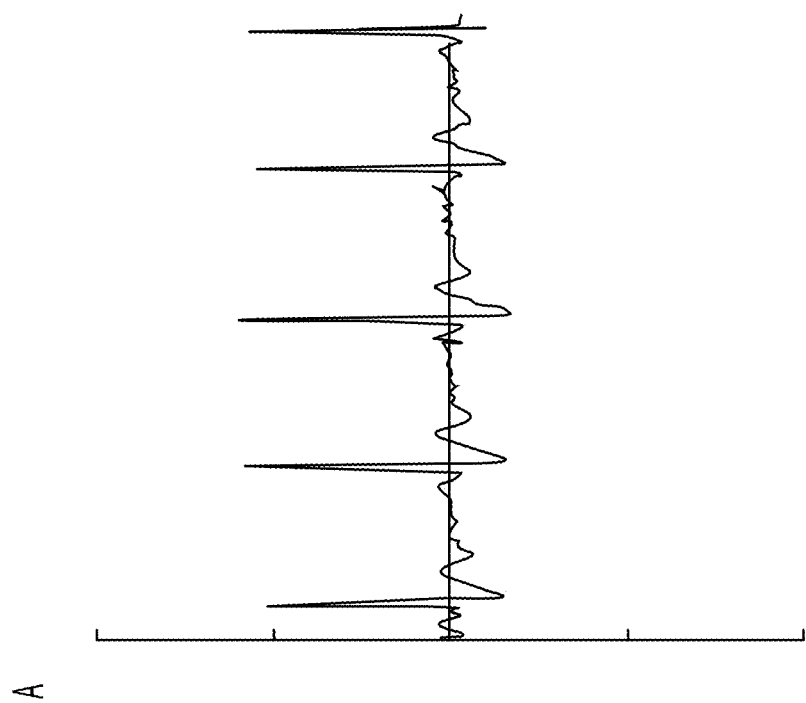

All recordings were obtained using NeuroNet VI software (Computational Diagnostics Inc., Pittsburgh, Pa., USA). FIG. 6 shows the two EKGs and demonstrates the ability to record EKGs of similar wave morphology and displacement using A) commercial electrodes or B) conductive polymer-coated polyester fibers.

It will be appreciated by persons skilled in the art that fibers described herein are not limited to what has been particularly shown and described. Rather, the scope of the fiber is defined by the claims which follow. It should further be understood that the above description is only representative of illustrative examples of embodiments. The description has not attempted to exhaustively enumerate all possible variations. The alternate embodiments may not have been presented for a specific portion of the fiber, and may result from a different combination of described portions, or that other un-described alternate embodiments may be available for a portion, is not to be considered a disclaimer of those alternate embodiments. It will be appreciated that many of those un-described embodiments are within the literal scope of the following claims, and others are equivalent.

The invention claimed is:

1. A conductive fiber comprising a fiber core and a coating thereon, wherein the coating comprises a polythiophene and a conductive carbon material, wherein the polythiophene is regioregular poly(3-hexylthiophene), further wherein the ratio between the regioregular poly(3-hexylthiophene) and the carbon material is selected so that the conductive fiber has an electrical resistance of less than about 0.8 kohm/cm.

2. The conductive fiber of claim 1, wherein the fiber core consists of a single filament fiber thread.

3. The conductive fiber of claim 1, wherein the fiber core comprises a nonconductive synthetic or natural polymer.

4. The conductive fiber of claim 1, wherein the fiber core consists essentially of cotton, nylon, silk, hemp, jute, flax, ramie, sisal, wool, or any combination thereof.

5. The conductive fiber of claim 1, wherein the fiber core comprises a polymer selected from polylactic acids, polyglycolic acids, polylactide-co-glycolide copolymers, polytrimethylene carbonate, poly-(ε)-caprolactone, poly-di-oxanone, polyhydroxyalkanoates, polyphosphasenes, polypropylene fumarates, polyanhydrides, polyorthoesters, polyimides, polyurethanes, polyurethaneureas, perfluoroalkoxy polymers, florinated ethylene/propylene copolymers, polyanhydride esters, polysaccharides, polyethylene-lactone copolymers, polyethylene-polyorthoester copolymers, hydrophilic vinyl polymers, phosphoryl cholines, hydroxamates, vinyl furanones, collagen, elastin, keratin, fibrin, and blends, copolymers, and homopolymers thereof.

6. The conductive fiber of claim 1, wherein the conductive carbon material is selected from the group consisting of graphene, multi-wall carbon nanotubes, single-wall carbon nanotubes, carbon black, graphite powder, graphene oxide, fullerenes, and any combination thereof.

7. The conductive fiber of claim 1, wherein the conductive carbon material consists essentially of single-wall carbon nanotubes.

8. The conductive fiber of claim 1, wherein the fiber core comprises one or more second groups selected from the group consisting of hydroxyl, amine, amide carboxylic, thiol, perfluoroalkyl, phosphonic acid and sulfonic acid.

9. The conductive fiber of claim 1, wherein the coating further comprises one or more conjugated polymers selected from the group consisting of poly(pyrrole), poly(aniline), poly(acetylene), poly(p-phenylene vinylene) (PPV), poly(3, 4-ethylene dioxythiophene)-poly(styrene sulfonate) (PEDOT-PSS).

10. The conductive fiber of claim 1, wherein the coating consists essentially of the regioregular poly(3-hexylthiophene) and the conductive carbon material.

11. The conductive fiber of claim 1, having an average diameter ranging from about 1 to about 10,000 microns.

12. The conductive fiber of claim 1, which is biocompatible and capable of delivering changes in electrical pulse and current.

13. An article of manufacture comprising the conductive fiber of claim 1.

14. The article of manufacture of claim 13, which is an implantable medical device.

15. The article of manufacture of claim 13, which is an electrode.

16. The conductive fiber of claim 1, wherein the polythiophene and the conductive carbon material are admixed with each other in the coating.

* * * * *